(12) United States Patent
Pentico et al.

(10) Patent No.: US 11,717,159 B2
(45) Date of Patent: Aug. 8, 2023

(54) PANORAMIC GONIOSCOPIC IMAGING

(71) Applicant: Optos Plc, Dunfermline (GB)

(72) Inventors: Clark Pentico, Simi Valley, CA (US); Brendan Hamel-Bissell, San Francisco, CA (US); Andre E. Adams, Tiburon, CA (US)

(73) Assignee: Optos Plc, Dunfermline (GB)

( * ) Notice: Subject to any disclaimer, the term of this patent is extended or adjusted under 35 U.S.C. 154(b) by 405 days.

(21) Appl. No.: 16/990,742

(22) Filed: Aug. 11, 2020

(65) Prior Publication Data

US 2021/0045632 A1    Feb. 18, 2021

Related U.S. Application Data

(60) Provisional application No. 62/885,581, filed on Aug. 12, 2019.

(51) Int. Cl.
*A61B 3/14* (2006.01)
*H04N 5/232* (2006.01)
*G02B 13/06* (2006.01)
*H04N 23/698* (2023.01)

(52) U.S. Cl.
CPC ............... *A61B 3/14* (2013.01); *G02B 13/06* (2013.01); *H04N 23/698* (2023.01)

(58) Field of Classification Search
CPC ........... G02B 13/06; A61B 3/117; A61B 3/14; H04N 5/23238
See application file for complete search history.

(56) References Cited

U.S. PATENT DOCUMENTS

| 4,134,647 A | 1/1979 | Ramos-Caldera |
| 2006/0050229 A1 | 3/2006 | Farberov |
| 2009/0185135 A1 | 7/2009 | Volk |
| 2010/0091244 A1 | 4/2010 | Volk |
| 2015/0002817 A1 | 1/2015 | Alasaarela et al. |
| 2017/0231491 A1 | 8/2017 | Tanassi et al. |

(Continued)

FOREIGN PATENT DOCUMENTS

EP    2866640 B1    1/2019

OTHER PUBLICATIONS

International Search Report and Written Opinion issued in corresponding application No. PCT/US2020/046015, dated Oct. 26, 2020.

(Continued)

*Primary Examiner* — Jack Dinh
(74) *Attorney, Agent, or Firm* — Faegre Drinker Biddle & Reath

(57) ABSTRACT

An imaging system may include a panoramic gonioscopic imaging apparatus that includes a disposable component configured to rest against a cornea of a patient, and an objective optical device configured to direct a continuous panoramic image of an entire circumference of an iridocorneal angle of the patient on an intermediate imaging plane, and a relay lens configured to direct the continuous panoramic image from the intermediate imaging plane to a sensor such that the sensor captures the entire circumference of the iridocorneal angle at once. The imaging system may also include a computing device in communication with the panoramic gonioscopic imaging apparatus, where the computing device configured to display an image of the entire circumference of the iridocorneal angle.

20 Claims, 7 Drawing Sheets

(56) References Cited

U.S. PATENT DOCUMENTS

2019/0200859 A1    7/2019   Ranchod

OTHER PUBLICATIONS

McNabb et al., Complete 360 circumferential gonioscopic optical coherence tomography imaging of the iridocorneal angle, Biomedical Optics Express, Mar. 20, 2015.
Perinchery et al., High resolution iridocorneal angle imaging system by axicon lens assisted gonioscoy, Scientific Reports, Jul. 29, 2016.
European Search Report dated Sep. 1, 2022 in European Patent Application No. 20 851 643 (9 sheets).

PANORAMIC GONIOSCOPIC IMAGING

FIELD

The application relates generally to devices for panoramic gonioscopic imaging of the eye.

BACKGROUND

The iridocorneal angle, or angle between the cornea and the iris at the point where the two meet, is useful in diagnosing and managing several medical conditions. The iridocorneal angle is typically evaluated using gonioscopy, a physician-performed procedure involving a gonioscopy prism that is placed against the anesthetized patient cornea and aligned with a slit lamp microscope.

The subject matter claimed herein is not limited to embodiments that solve any disadvantages or that operate only in environments such as those described above. Rather, this background is only provided to illustrate one example technology area where some embodiments described herein may be practiced.

SUMMARY

One or more embodiments of the present disclosure include a panoramic gonioscopic imaging apparatus including a disposable lens which is configured to rest against a cornea of a patient or against an optically clear fluid on the cornea of the patient. The apparatus may include an objective optical device configured to place a continuous panoramic image of an iridocorneal angle of the patient on an intermediate imaging plane and a relay lens configured to relay the continuous panoramic image from the intermediate imaging plane to a sensor. The objective optical device may be reflective or refractive. The relay lens may include an aperture or shutter.

One or more additional embodiments of the present disclosure may include an imaging system that may include a panoramic gonioscopic imaging apparatus that includes a disposable component configured to rest against a cornea of a patient, and an objective optical device configured to direct a continuous panoramic image of an entire circumference of an iridocorneal angle of the patient on an intermediate imaging plane, and a relay lens configured to direct the continuous panoramic image from the intermediate imaging plane to a sensor such that the sensor captures the entire circumference of the iridocorneal angle at once. The imaging system may also include a computing device in communication with the panoramic gonioscopic imaging apparatus, where the computing device configured to display an image of the entire circumference of the iridocorneal angle.

BRIEF DESCRIPTION OF FIGURES

Example embodiments will be described and explained with additional specificity and detail through the use of the accompanying drawings in which.

DESCRIPTION OF EMBODIMENTS

The present disclosure relates to, inter alia, devices for panoramic gonioscopic imaging of the eye. Gonioscopy usually involves a physician placing a gonioscopy prism against the anesthetized patient cornea and aligning it with a slit lamp microscope. The gonioscopy prism typically has 4 to 6 flat prism mirrors, each allowing the physician to view one portion of the circumferential iridocorneal angle tissue. The physician looks through each mirror sequentially in order to evaluate the full 360 degrees of the iridocorneal angle, which is time-consuming, technically difficult, and uncomfortable for the patient. The physician makes notes using standardized notations for gonioscopic evaluation. While slit lamp smart phone adapters exist to allow photographic imaging of the iridocorneal angle via gonioscopy, several photos must be taken and stitched together to provide a panoramic view of the iridocorneal angle. This requires processing power, is prone to alignment error, and introduces a delay between each photo. A continuous photographic evaluation of the 360 degrees of the iridocorneal angle (e.g., capturing the entire circumference of the iridocorneal angle in a single image) would improve medical eye care by providing an objective, repeatable, detailed, comprehensive, and simple way to evaluate the iridocorneal angle, either as a supplement to, or in place of, physician gonioscopic evaluation.

For example, a disposable component like a steep, curved disposable lens may be placed against a patient's cornea or on a thin layer of optically clear fluid upon the cornea of a patient. The disposable component may allow light from a full 360 degrees of the iridocorneal angle to escape the eye (e.g., a ring of light depicting the entire iridocorneal angle about the entire eye). The light from the 360 degrees of the iridocorneal angle may then pass through a rotationally symmetric objective lens or be reflected by a rotationally symmetric reflective device which may direct the light to an intermediate imaging plane. The light from the 360 degrees of the iridocorneal angle may form a panoramic image of the iridocorneal angle at the intermediate imaging plane (e.g., in a ring shape). A relay lens (which may or may not also be rotationally symmetric) may transmit the intermediate panoramic image of the iridocorneal angle to a sensor which may capture the panoramic image of the full iridocorneal angle.

Figure 1A:
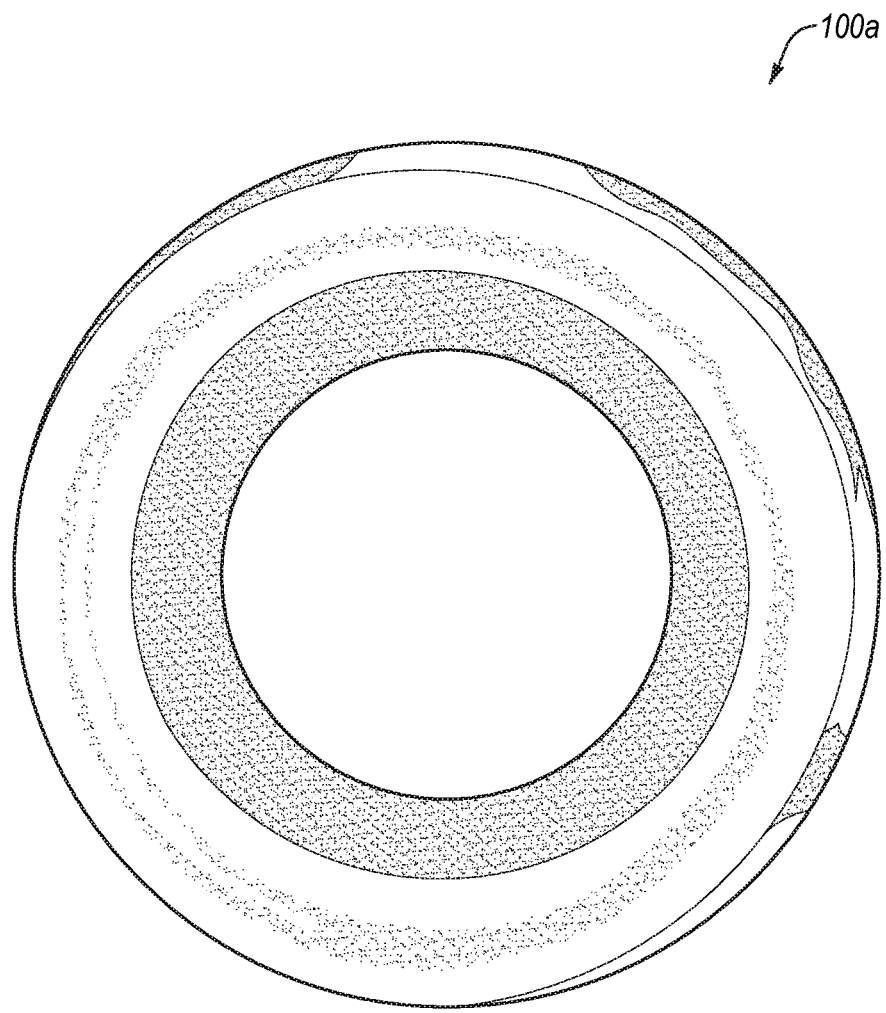
FIGS. 1A and 1B illustrate example images of the entire circumference of an iridocorneal angle, in a circular representation and in a linear representation, respectively.
Figure 1B:

FIGS. 1A and 1B illustrate example images of the entire circumference of an iridocorneal angle, in a circular representation and in a linear representation, respectively. For example, an image 100a may represent the circular image captured of the entire iridocorneal angle. An image 100b may represent the entire iridocorneal angle in a linear manner, rather than in a circle. For example, image processing may be applied to the image 100a to break the ring along a radial line and stretch, skew, etc. the image 100*a* to present the circular image of 100*a* in the linear representation 100*b* of FIG. 1B.

Figure 2A:
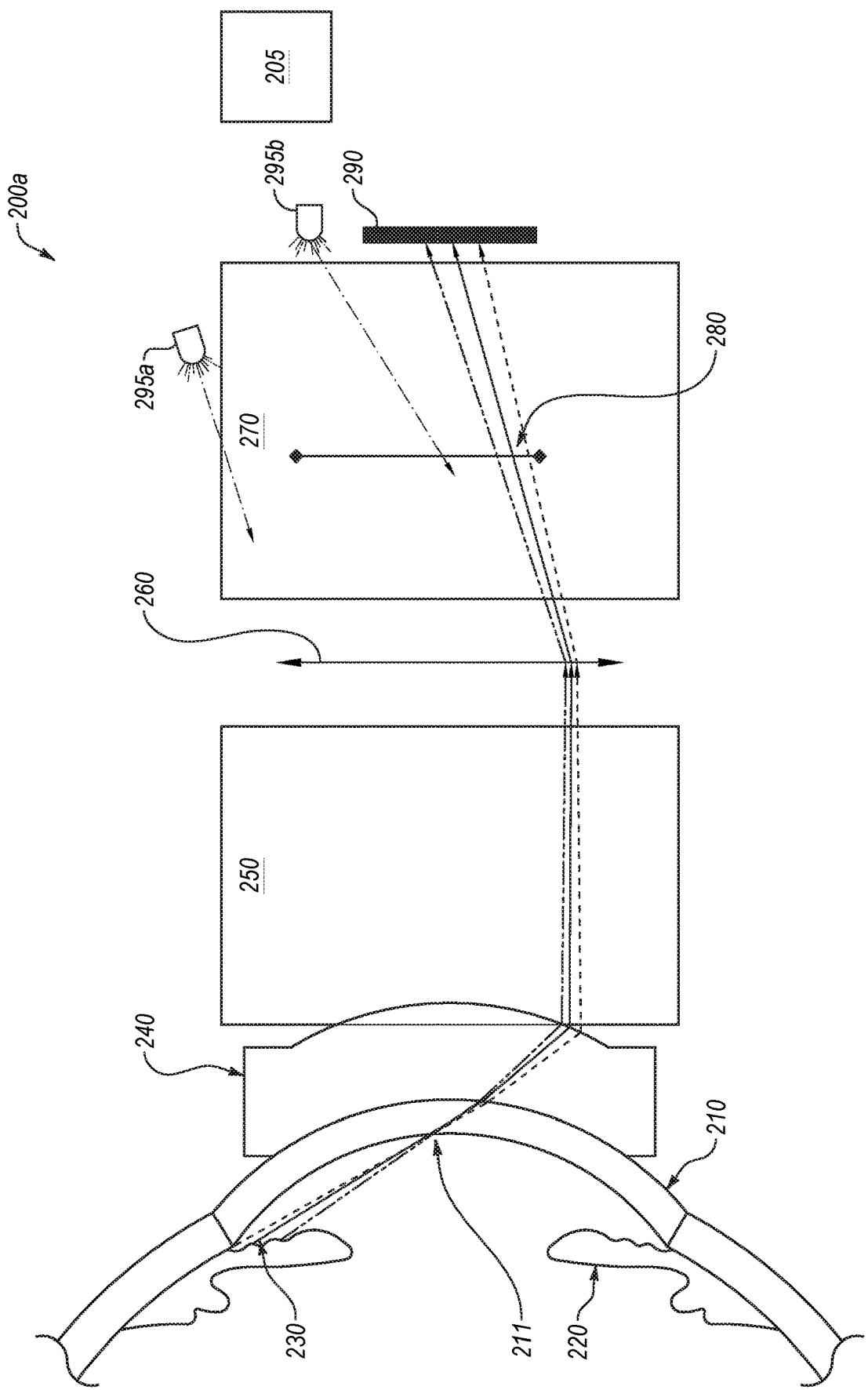
FIG. 2A illustrates an example of a gonioscopic imaging apparatus.

FIG. 2A illustrates an example gonioscopic imaging apparatus 200*a*, in accordance with one or more embodiments of the present disclosure. The gonioscopic imaging apparatus 200*a* may include a disposable component 240, an objective optical device 250, a relay lens 270, a sensor 290, and/or one or more illumination sources 295 (such as 295*a/b*).

In some embodiments, the disposable component 240 may include a disposable lens (such as a disposable contact lens), an optically neutral window or sleeve, etc. In some embodiments, the disposable component 240 may rest upon a cornea 210 of the eye of the patient. There may be a thin layer of optically clear fluid such as natural tear film of the eye or a synthetic lubrication fluid between the disposable component 240 and the cornea 210. The iridocorneal angle 230 is formed at the point where the iris 220 and the cornea 210 meet. Light rays 211 that reflect off the iridocorneal angle 230 to permit imaging of the iridocorneal angle 230 would normally be trapped within the eye by total internal reflection due to the sharp angle at which the light rays 211 contact the surface of the cornea 210. Contact between the cornea 210 and the disposable component 240, however, may allow the light rays 211 to escape the eye, making imaging of the iridocorneal angle 230 possible.

In some embodiments, the light rays 211 may be received at the objective optical device 250 from the disposable component 240. The objective optical device may be shaped and configured to transmit the light rays 211 for imaging the iridocorneal angle 230 from the disposable component 240 to an intermediate imaging plane 260 where the light rays 211 may form a ring-shaped image of the entire iridocorneal angle 230 about the entire eye.

The objective optical device 250 may take a variety of shapes and configurations. FIGS. 3A-3B and 4A-4B illustrate various embodiments of the object optical device 250. In FIG. 2A, the objective optical device 250 is shown only as an element of the gonioscopic imaging apparatus 200*a* located between the disposable component 240 and the intermediate imaging plane 260. In some embodiments, the objective optical device 250 may include a plurality of lenses and/or mirrors. When imaging the iridocorneal angle 230, the objective optical device 250 may transmit, direct, reflect, or otherwise convey the light rays 211 for imaging the iridocorneal angle 230 to the intermediate imaging plane 260, but this is not a limit to its functionality. The objective optical device 250 may contain a central area and a peripheral area. The peripheral area of the objective optical device 250 may transmit, direct, reflect, or otherwise convey the image of the iridocorneal angle 230 to the intermediate imaging plane 260, and the central area of the objective optical device 250 may do the same or may be used for another purpose, such as imaging the iris 220, the lens of the eye (not shown), and/or the surrounding tissue of the iris and lens.

In some embodiments, the relay lens 270 may transmit the image of the iridocorneal angle 230 as rendered at the intermediate imaging plane 260 to a sensor 290. The relay lens 270 may include an aperture 280 which may act as a shutter for the sensor 290. In some embodiments, the aperture 280 may act as a baffle or other optically limiting device to limit the image being captured such that the image is focused on the iridocorneal angle 230.

In some embodiments, the central area of the objective optical device 250 and/or the relay lens 270 may contain a central imaging pathway for imaging the iris, lens, and/or adjacent tissues in the eye. The central imaging pathway may use the same sensor 290 and/or optical components as the light rays 211 for imaging the iridocorneal angle 230. Additionally or alternatively, the objective optical device 250 and/or the relay lens 270 may be hollow or otherwise have a void in material through the central region of the gonioscopic imaging apparatus 200*a*. In these and other embodiments, the central imaging pathway may include a separate sensor and/or one or more separate optical components. In some embodiments, the hollow or void in the central area of the objective optical device 250 may additionally or alternatively contain structural elements. For example, the central area of the objective lens could be used for nesting different optical components of the objective optical device 250 or it could contain structural elements for positioning the gonioscopic imaging apparatus 200*a*.

In some embodiments, the gonioscopic imaging apparatus 200*a* may have the ability to image panoramic views of the entire circumference of the iridocorneal angle 230 using a single imaging pathway. The objective optical device 250 may be rotationally symmetric about an axis extending outwards from the pupil of the eye, thereby permitting imaging of the entire iridocorneal angle 230. The objective optical device 250 may have a donut-shaped field of view. For example, the objective optical device 250 may take the form of an asphere or a toroidal surface. With a donut-shaped, rotationally symmetric field of view, the objective optical device 250 may transmit to the intermediate imaging plane 260 the light rays 211 from a full three hundred and sixty degrees of the iridocorneal angle 230. In such a case, the intermediate imaging plane 260 may receive a panoramic image of the iridocorneal angle 230. In some embodiments, the panoramic image may also include the zonules when the pupil of the eye is adequately dilated. For example, the image of the iridocorneal angle and/or images from the central region of the objective optical device 250 may facilitate capturing images of the zonules.

In some embodiments, the intermediate image plane 260 may represent the field stop version of the image of the iridocorneal angle 230. For example, one or more walls, baffles, etc. may be used to constrict and/or otherwise limit the light rays 211 provided to the relay lens 270 to be those which depict the iridocorneal angle 230 at the intermediate image plane 260.

In some embodiments, illumination sources 295 may provide any type of illumination to the iridocorneal angle 230 and/or the eye generally to facilitate imaging of the iridocorneal angle 230 and/or other parts of the eye. Such illumination may be diffuse, patterned, or combinations thereof. For example, the illumination may be provided by a continuous circumferential light source (such as a ring of adjacent sources, or a non-circumferential light source that is optically projected as a circumferential source using optical components) or by multiple distinct point sources. The illumination may be coaxial with the imaging pathway or non-coaxial, or a combination of illumination sources providing illumination in both coaxial and non-coaxial pathways. For example, the illumination may comprise coaxial diffuse illumination and angled patterned illumination.

In some embodiments, a separate illumination source 295 may be directed through the pupil of the eye to induce constriction of the pupil. The separate illumination source 295 may be separately adjustable relative to the iridocorneal illumination. In these and other embodiments, sequential panoramic images of the iridocorneal angle 230 may be taken with varying levels of illumination through the pupil to cause the pupil to dilate to different levels while panoramic images of the iridocorneal angle 230 are captured. Such a series of images may provide dynamic information about the iridocorneal angle 230 as it changes due to pupil constriction. Additionally or alternatively, sequential panoramic images of the iridocorneal angle 230 may be beneficial in guiding the panoramic gonioscopic imaging apparatus 200a into position by providing real-time feedback.

In some embodiments, the gonioscopic imaging apparatus 200a may include a computing device 205 that may facilitate performance of the various operations described according to the present disclosure. For example, the computing device 205 may cause the illumination sources 295 to change direction, frequency, magnitude, level, etc. of the illumination provided. As another example, the computing device 205 may trigger the sensor 290 to capture data as a captured image. As a further example, the computing device 205 may synchronize the illumination sources 295 and/or the sensor 290 to capture images in conjunction with changes in illumination. In some embodiments, the computing device 205 may combine various images in certain ways and/or may present those images to a user (such as a clinician).

In some embodiments, the computing device 205 may include a processor, a memory, etc. and may be in communication with and/or part of the panoramic gonioscopic imaging apparatus 200a.

Generally, the processor may include any suitable special-purpose or general-purpose computer, computing entity, or processing device including various computer hardware or software modules and may be configured to execute instructions stored on any applicable computer-readable storage media. For example, the processor may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data.

It is understood that the processor may include any number of processors distributed across any number of networks or physical locations that are configured to perform individually or collectively any number of operations described herein. In some embodiments, the processor may interpret and/or execute program instructions and/or processing data stored in the memory. By interpreting and/or executing program instructions and/or process data stored in the memory, the device may perform operations, such as the operations performed by the panoramic gonioscopic apparatuses described in the present disclosure.

The memory may include computer-readable storage media or one or more computer-readable storage mediums for carrying or having computer-executable instructions or data structures stored thereon. Such computer-readable storage media may be any available media that may be accessed by a general-purpose or special-purpose computer, such as the processor. By way of example, and not limitation, such computer-readable storage media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable storage media. In these and other embodiments, the term "non-transitory" as used herein should be construed to exclude only those types of transitory media that were found to fall outside the scope of patentable subject matter in the Federal Circuit decision of In re Nuijten, 500 F.3d 1346 (Fed. Cir. 4007). In some embodiments, computer-executable instructions may include, for example, instructions and data configured to cause the processor to perform a certain operation or group of operations as described in the present disclosure.

Modifications, additions, or omissions may be made to the gonioscopic imaging apparatus 200a without departing from the scope of the present disclosure. For example, the gonioscopic imaging apparatus 200a may include more or fewer elements than those illustrated in FIG. 2A. For example, the objective optical device 250 and the relay lens 270 may comprise one or more lenses and mirrors.

Figure 2C:
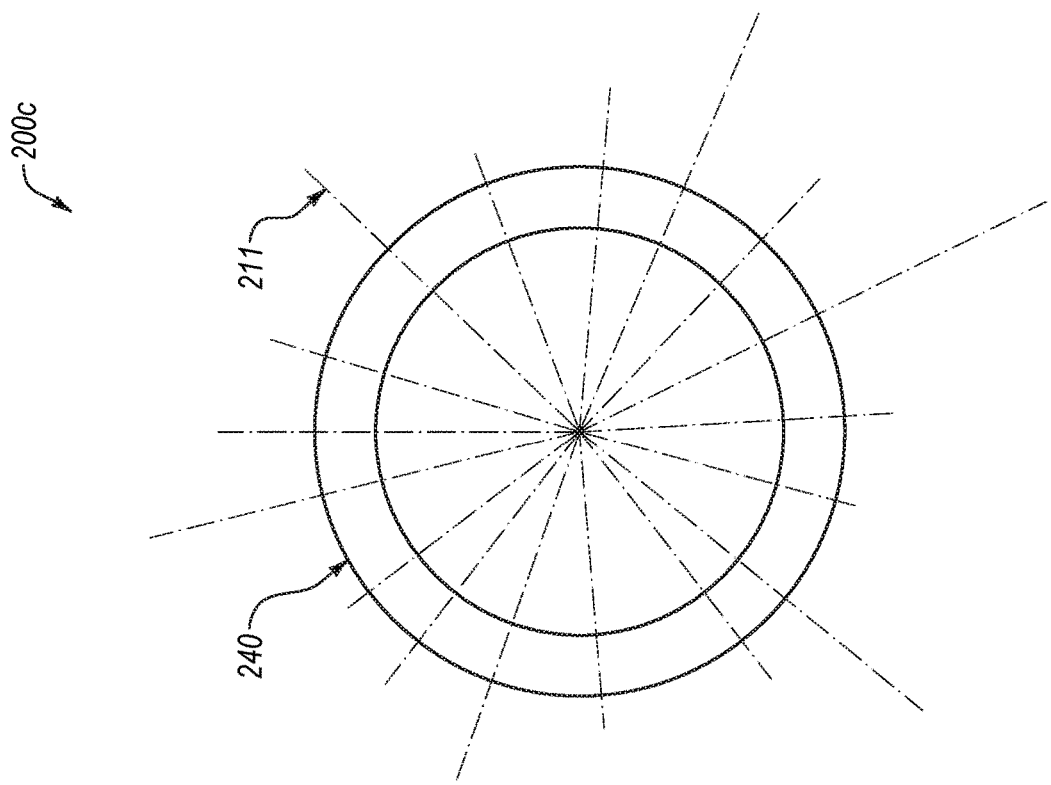
FIGS. 2B and 2C illustrate a side view and a front view, respectively, of portions of the gonioscopic imaging apparatus of FIG. 2A.
Figure 2B:
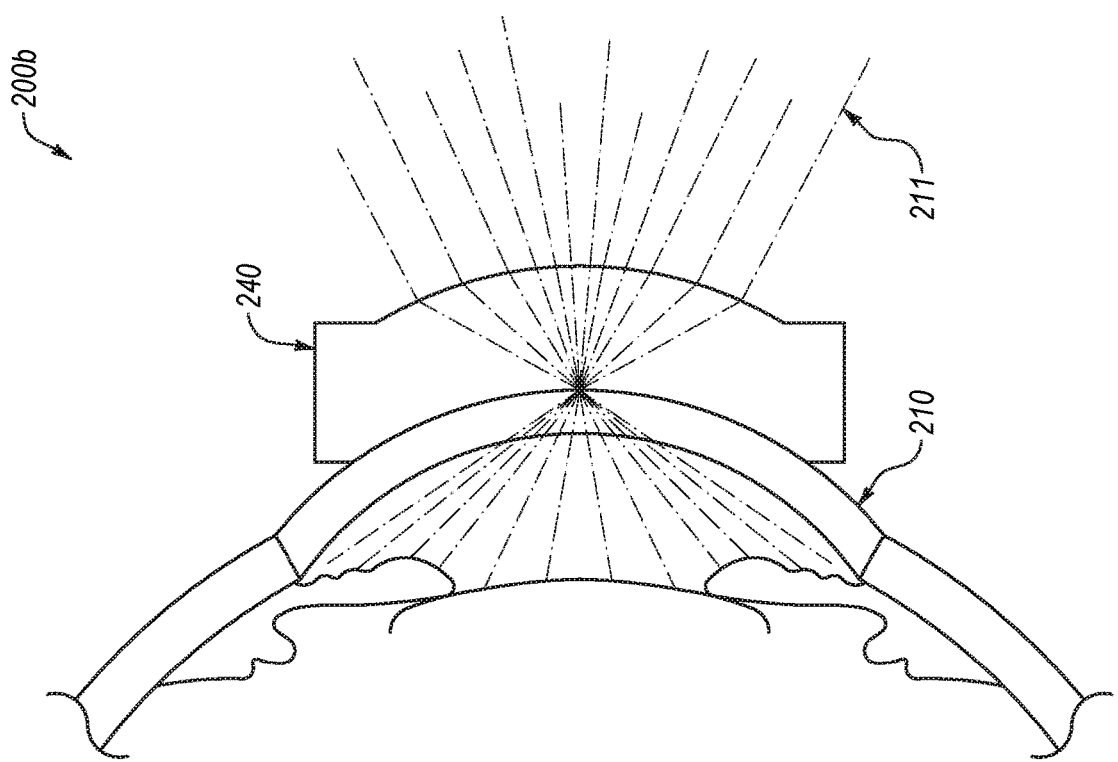

FIGS. 2B and 2C illustrate a side view and a front view, respectively, of portions of the gonioscopic imaging apparatus 200b and 200c, corresponding to the gonioscopic imaging apparatus 200a of FIG. 2A, in accordance with one or more embodiments of the present disclosure. FIGS. 2B and 2C illustrates the light rays 211 such that the rotationally symmetrical nature of the light rays 211 is understood. For example, the light rays 211 may extend outward in a radiating manner from the disposable component 240 in a full three hundred and sixty degrees corresponding to the entire circumference of the iridocorneal angle.

Figure 3A:
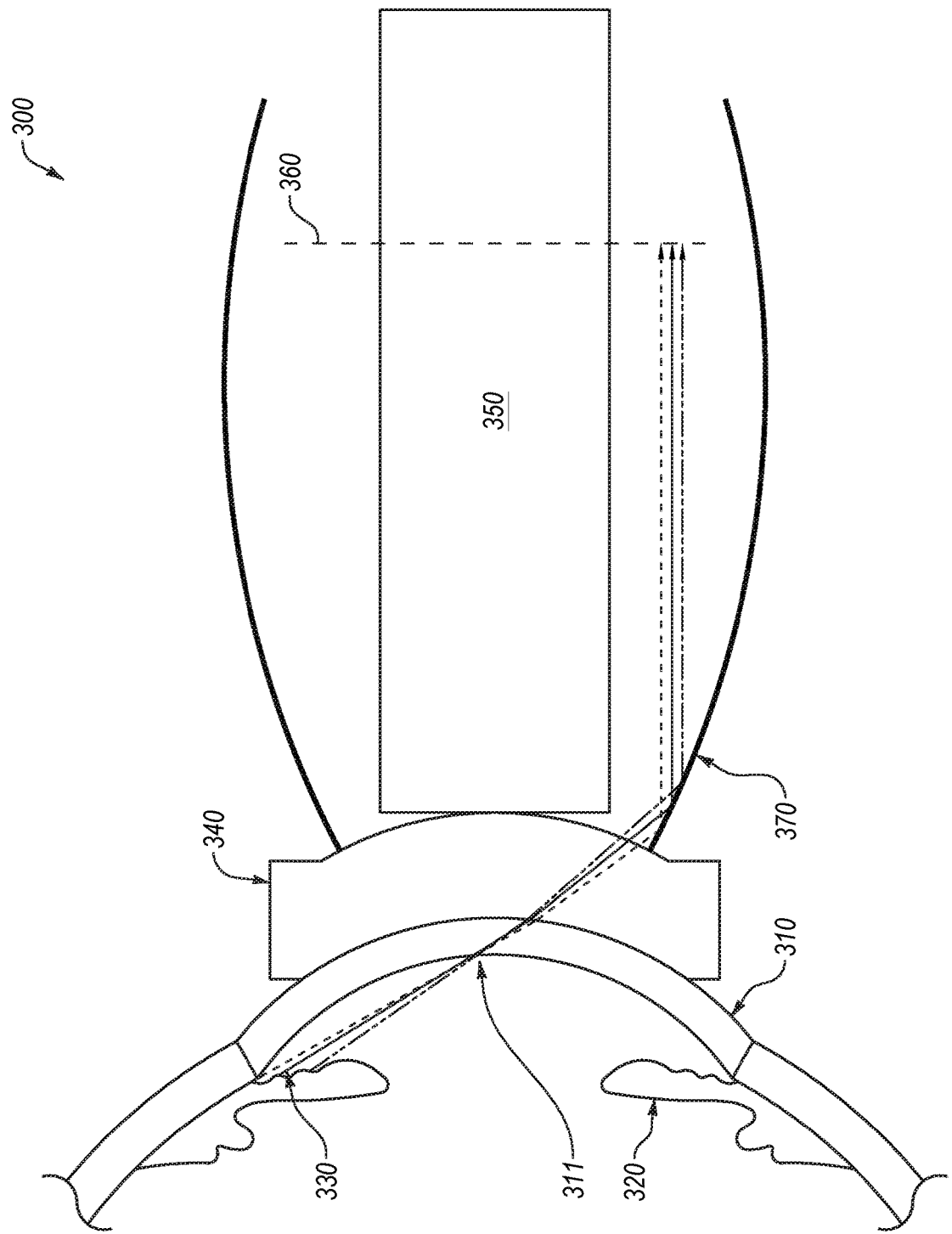
FIG. 3A illustrates an example panoramic gonioscopic imaging apparatus with a reflective objective optical device.

FIG. 3A illustrates an example panoramic gonioscopic imaging apparatus 300 with a reflective objective optical device, in accordance with one or more embodiments of the present disclosure. As illustrated in FIG. 3, the cornea 310, iris 320, light rays 311, iridocorneal angle 330, and/or disposable component 340 may be similar or comparable to the cornea 210, iris 220, light rays 211, iridocorneal angle 230, and/or disposable component 240 of FIG. 2. The light rays 311 from the iridocorneal angle 330 may exit the eye, pass through the disposable component 340 and reflect off a reflector surface 370. The reflector surface 370 may be an example implementation and/or component of the objective optical device 250 as illustrated in FIG. 2. The reflector surface 370 may include one or more reflective surfaces and/or refractive lenses for directing, reflecting, transmitting or otherwise conveying the light rays 311 to an intermediate imaging plane 360.

In some embodiments, a central area of the gonioscopic imaging apparatus 300 may include central objective lens(es) 350 and a peripheral area with the reflector surface 370. The peripheral area of the gonioscopic imaging apparatus 300 with the reflector surface 370 may direct the light rays 311 for imaging the iridocorneal angle 330 to the intermediate imaging plane 360. Additionally or alternatively, the central area of the gonioscopic imaging apparatus 300 may facilitate imaging of the iris, lens, and/or surrounding tissue.

The reflector surface 370 may take the form of a rotationally symmetric surface and have a donut-shaped field of view. For example, the reflector surface 370 may take the form of an asphere with the inner surface mirrored or otherwise reflective. The reflector surface 370 may also take the form of a toroidal surface, including a partial toroidal surface (e.g., with open regions proximate the eye to allow the light rays 311 to pass into the interior of the toroidal surface and/or open regions proximate the sensor (not shown) to permit the light rays 311 to proceed to the sensor) with the inner surface mirrored or otherwise reflective. In some embodiments in which the reflector surface 370 is a toroidal shape, the rotational axis of the toroid may fall between the disposable component 340 and the intermediate imaging plane 360. As another example, the reflector surface 370 may take the form of a spherical segment, a truncated sphere, an ellipsoid segment, a truncated ellipsoid, etc. where the internal surface may be reflective. The periphery of the reflector surface 370 may include a reflector surface for directing the light rays 311 from the iridocorneal angle 330 to the intermediate imaging plane 360. In some embodiments, the reflector surface 370 may be shaped and positioned such that the light rays 311 may be telecentric at the intermediate imaging plane 360 (e.g., the light rays 311 may be generally parallel with the optical axis of the gonioscopic imaging apparatus 300 and/or the eye).

In some embodiments, the reflector surface 370 may include multiple reflective surfaces rather than a single mirrored surface. Additionally or alternatively, the reflector surface 370 may include a hybrid reflector with some refractive surfaces in addition to the reflective surface or surfaces.

Following the intermediate imaging plane 360, a relay lens may transmit the light rays 311 to a sensor, for example, as shown in FIG. 2.

In some embodiments, the central objective lens(es) 350 may contain a central imaging pathway for imaging the iris, lens, and/or adjacent tissues in the eye. The central imaging pathway may use the same sensor and/or optical components as the light rays 311 for imaging the iridocorneal angle 330 or it may use a separate sensor and/or optical components. In some embodiments, the central area of the gonioscopic imaging apparatus 300 may include structural elements. For example, the central area may be used for nesting different optical components of the central objective lens 350 and/or the reflector surface 370. Additionally or alternatively, the central area may contain structural elements for positioning the gonioscopic imaging apparatus 300.

Modifications, additions, or omissions may be made to FIG. 3A without departing from the scope of the present disclosure. For example, the reflector surface 370 may comprise multiple reflective surfaces and/or refractive lenses. As another example, the reflector surface 370 may take the form of any rotationally symmetric surface.

Figure 3B:
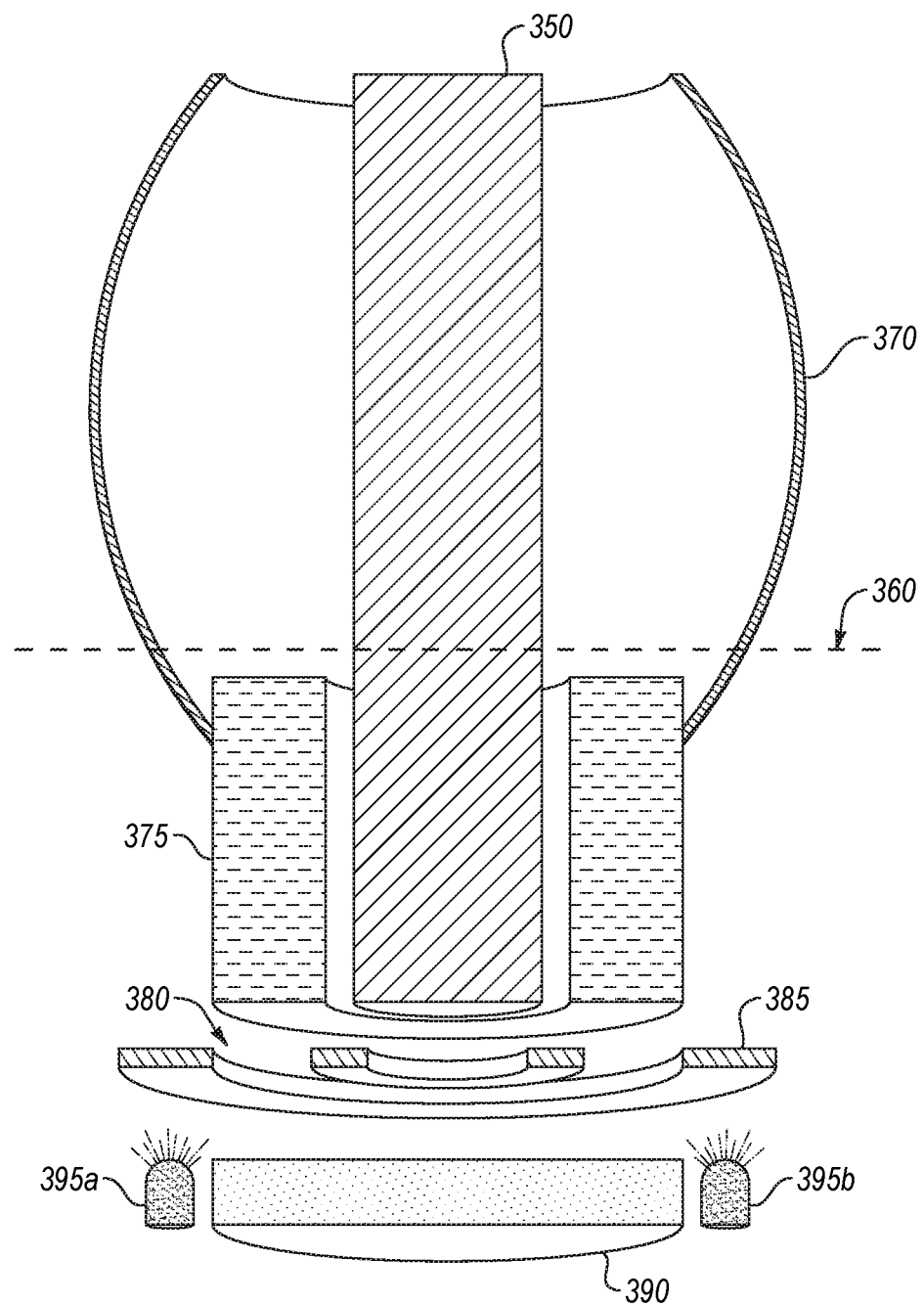
FIG. 3B illustrates a cutaway view of portions the example panoramic gonioscopic imaging apparatus of FIG. 3A.

FIG. 3B illustrates a cutaway view of portions the example panoramic gonioscopic imaging apparatus 300 of FIG. 3A, in accordance with one or more embodiments of the present disclosure. The relay lens 375, the aperture 380, the sensor 390, and the illumination sources 395a/395b may be similar and/or comparable to the relay lens 270, the aperture 280, the sensor 290, and the illumination sources 295a/295b as illustrated in FIG. 2A, respectively. For example, the relay lens 375 may direct the light rays 311 (not shown) at the intermediate imaging plane 360 to the sensor 390. As another example, the aperture 380 may act as a shutter for the sensor 390. As a further example, the illumination sources 395a/395b may operate to provide various types of illumination to the iridocorneal angle, such as various frequencies of illumination, various types of indirect/direct illumination, etc.

As illustrated in FIG. 3B, the reflector surface 370 may have a toroidal and/or aspherical shape with a reflective inner surface.

In some embodiments, the aperture 380 may be formed by walls 385 and/or baffles or other physical structure to absorb or block certain light rays 311 within the gonioscopic imaging apparatus 300.

While the central objective lens 350 and/or the relay lens 375 are illustrated as large generally cylindrical shaped bodies, it will be appreciate that they can take any shape or form with various curvatures on their respective surfaces to facilitate directing various light rays and/or directing light in the manner described in the present disclosure. Additionally or alternatively, the central objective lens 350 and/or the relay lens 375 may be divided into multiple individual components positioned within the general region indicated by the central objective lens 350 and/or the relay lens 375.

Figure 4A:
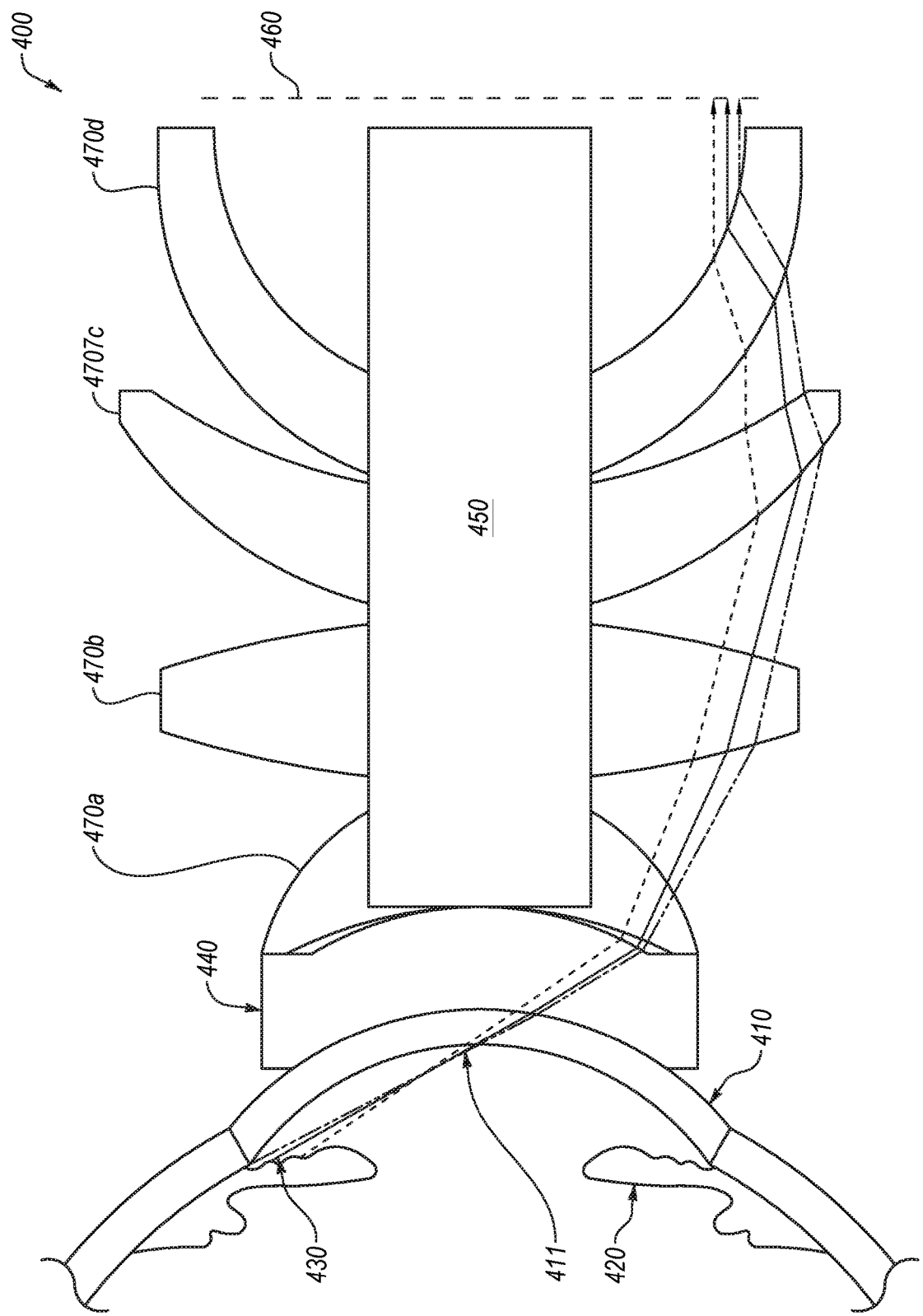
FIG. 4A illustrates an example panoramic gonioscopic imaging apparatus with a refractive objective optical device.

FIG. 4A illustrates an example of a panoramic gonioscopic imaging apparatus 400 with a refractive objective lens, in accordance with one or more embodiments of the present disclosure. For example, the panoramic gonioscopic imaging apparatus 400 illustrated in FIG. 4A may include one or more peripheral objective lenses 470 in addition to or alternative to the reflector surface 370 of FIG. 3A. As illustrated in FIG. 4A, the cornea 410, iris 420, light rays 411, iridocorneal angle 430, and/or disposable component 440 may be similar or comparable to the cornea 210, iris 220, light rays 211, iridocorneal angle 230, and/or disposable component 240 of FIG. 2A. The light rays 411 from the iridocorneal angle 430 may exit the eye, pass through the disposable component 440 and pass through one or more peripheral objective lenses 470. The peripheral objective lenses 470 may include one or more refractive lenses for transmitting, directing, and/or otherwise conveying the light rays 411 to an intermediate imaging plane 460.

Each of the peripheral objective lenses 470 may take the form of a rotationally symmetric surface or lens with a donut-shaped field of view. In these and other embodiments, the peripheral objective lenses 470 may include refractive components for transmitting or otherwise directing the light rays 411 from the iridocorneal angle 430 to the intermediate imaging plane 460. In some embodiments, the peripheral objective lenses 470 may direct the light rays 411 along the periphery of the gonioscopic imaging apparatus 400, rather than directing them through the central region of the gonioscopic imaging apparatus 400.

In some embodiments, the peripheral objective lenses 470 may be shaped and/or positioned such that the light rays 411 may be telecentric at the intermediate imaging plane 460. Following the intermediate imaging plane 460, a relay lens (not shown) may transmit the light rays 411 to a sensor (not shown), such as described with reference to FIG. 2A.

In some embodiments, the peripheral objective lenses 470 may be shaped and/or positioned to transmit, direct, or otherwise convey the light rays 411 from one peripheral objective lens 470 to a next peripheral objective lens 470 in a cascade or series of lenses until the light rays 411 are directed transmitted, directed, or otherwise conveyed to the intermediate imaging plane 460. In some embodiments, the cascade or series of lenses may be continued until the light rays are telecentric at the intermediate imaging plane 460.

In some embodiments, a central area of the objective lens may include the central objective lens 450 that may be used to facilitate a central imaging pathway for imaging the iris, lens, and/or adjacent tissues in the eye. The central imaging pathway may use the same sensor and/or optical components as the light rays 411 for imaging the iridocorneal angle 430 or it may use a separate sensor and/or optical components. The central area may additionally or alternatively contain structural elements. For example, the central area may be used for nesting different optical components associated with the central and/or peripheral objective lens(es) 450/470 or it could contain structural elements for positioning the gonioscopic imaging apparatus 400.

Modifications, additions, or omissions may be made to FIG. 4A without departing from the scope of the present disclosure. For example, the peripheral objective lenses 470 may include multiple refractive lenses which may take many shapes.

Figure 4B:
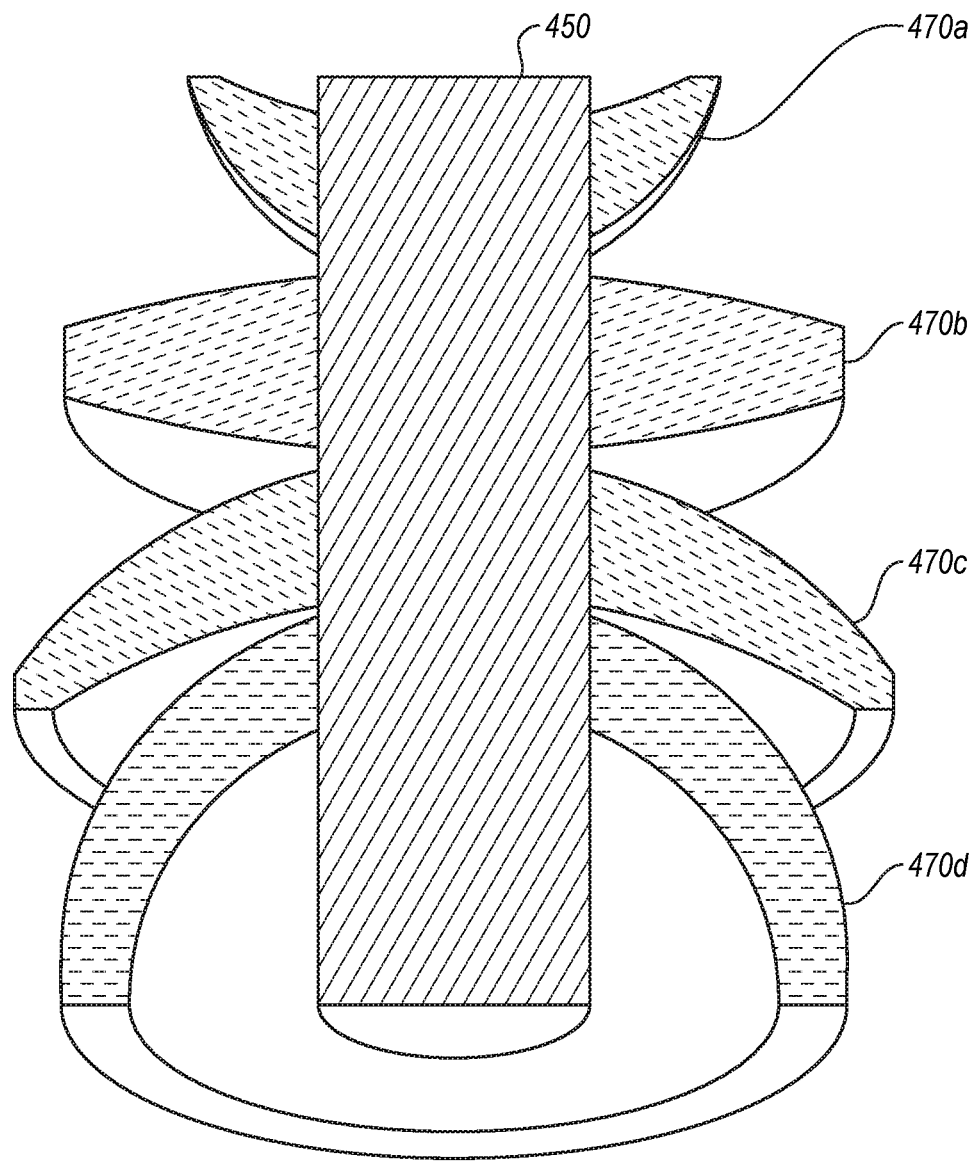
FIG. 4B illustrates a cutaway view of portions the example panoramic gonioscopic imaging apparatus of FIG. 4A.

FIG. 4B illustrates a cutaway view of portions the example panoramic gonioscopic imaging apparatus 400 of FIG. 4A, in accordance with one or more embodiments of the present disclosure. For example, FIG. 4B illustrates an example of a cascade of peripheral objective lenses 470, including the lenses 470a-470d. As can be seen in the cut away view, each of the lenses 470a-d may be individually rotationally symmetrical about the optical axis of the panoramic gonioscopic imaging apparatus 400. Additionally, they may be shaped such that the central region of each of the lenses 470a-d includes a void/hole such that the central objective lens 450 may be disposed therein. Additionally, it may be observed that the lenses 470a-d may or may not be partially nested within each other.

In some embodiments, the panoramic gonioscopic apparatuses 200a-c, 300, and/or 400 of FIGS. 2A-4B, respectively, may rapidly acquire sequential panoramic images of the iridocorneal angle. In some embodiments, the sequential panoramic images may provide information about the iridocorneal angle in different conditions such as different illumination levels, different spectra and/or different focus positions. For example, sequential panoramic images of the iridocorneal angle captured with different illumination levels may be processed or stacked to increase the dynamic range of a single image. As another example, sequential panoramic images of the iridocorneal angle captured at different focal planes may be used to create an enhanced depth of field. In some embodiments, sequential panoramic images may allow for stacking of multiple images taken in similar conditions to improve the signal to noise ratio of a composite image. In some embodiments, sequential panoramic images of the iridocorneal angle captured with different frequencies of illumination may be used to enhance viewing and/of identification of different features, aspects, or landmarks in the iridocorneal angle.

In some embodiments, a series of images may be taken in rapid succession with differing levels of illumination of the iridocorneal angle itself. Such images may be processed and/or stacked such that the dynamic range of a single image may be enhanced and/or increased. For example, a clinician may observe, at their leisure, the sequentially stacked images with varying illumination to observe the iridocorneal angle subjected to different wavelengths/spectrums of illumination, different intensities of illumination, etc.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method. For example, the dashed lines of the illumination paths and imaging paths are not meant to reflect an actual optical design, but are illustrative of the concepts of the present disclosure.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner. Additionally, the term "about" or "approximately" should be interpreted to mean a value within 10% of actual value.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

The invention claimed is:

1. A panoramic gonioscopic imaging apparatus comprising:
    a disposable component configured to rest against a cornea of a patient;
    an objective optical device configured to direct a continuous panoramic image of an entire circumference of an iridocorneal angle of the patient on an intermediate imaging plane; and
    a relay lens configured to direct the continuous panoramic image from the intermediate imaging plane to a sensor such that the sensor captures the entire circumference of the iridocorneal angle at once.

2. The panoramic gonioscopic imaging apparatus of claim 1, further comprising an illumination source configured to illuminate the iridocorneal angle as the sensor captures the entire iridocorneal angle.

3. The panoramic gonioscopic imaging apparatus of claim 2, wherein the illumination source provides illumination that is one of diffuse, patterned, or a combination thereof.

4. The panoramic gonioscopic imaging apparatus of claim 3, wherein the illumination source provides illumination that includes diffuse coaxial illumination and angled patterned illumination.

5. The panoramic gonioscopic imaging apparatus of claim 2, further comprising:
    a second illumination source aimed through a pupil of the patient; and
    a controller in communication with the second illumination source and the sensor, the controller configured to cause varying levels of illumination to be provided by the second illumination source while the sensor captures successive images such that the successive images capture the iridocorneal angle with varying levels of pupil dilation.

6. The panoramic gonioscopic imaging apparatus of claim 2, further comprising a controller in communication with the illumination source and the sensor such that successive images are captured with different levels of illumination to be stacked for an increased dynamic range compared to a single captured image.

7. The panoramic gonioscopic imaging apparatus of claim 2, further comprising a controller in communication with the illumination source and the sensor such that successive images are captured with different frequencies of illumination in the successive images.

8. The panoramic gonioscopic imaging apparatus of claim 2, further comprising a controller in communication with the illumination source and the sensor such that successive images are captured with different focal planes in the successive images to be combined for an increased depth of field compared to a single captured image.

9. The panoramic gonioscopic imaging apparatus of claim 1, wherein the objective optical device comprises a reflective device shaped and positioned to reflect light rays for imaging the iridocorneal angle off of an inside surface of the reflective device towards the intermediate imaging plane.

10. The panoramic gonioscopic imaging apparatus of claim 9, wherein the reflective device is an aspherical or toroidal shape.

11. The panoramic gonioscopic imaging apparatus of claim 9, further comprising one or more refractive elements to direct the light rays to the intermediate imaging plane.

12. The panoramic gonioscopic imaging apparatus of claim 1, wherein the objective optical device comprises one or more refractive lenses shaped and positioned to direct light rays for imaging the iridocorneal angle towards the intermediate imaging plane.

13. The panoramic gonioscopic imaging apparatus of claim 12, wherein the one or more refractive lenses includes at least three lenses that are each individually rotationally symmetric.

14. The panoramic gonioscopic imaging apparatus of claim 1, wherein the objective optical device is hollow along a central axis such that light rays for imaging the iridocorneal angle are directed along a periphery of the panoramic gonioscopic imaging apparatus.

15. The panoramic gonioscopic imaging apparatus of claim 14, further comprising one or more optical elements disposed along the central axis for imaging an iris, lens, or surrounding tissue of the patient.

16. The panoramic gonioscopic imaging apparatus of claim 15, wherein a central imaging pathway for imaging the iris, lens, or surrounding tissue shares one or more lenses with a peripheral imaging pathway for imaging the iridocorneal angle.

17. The panoramic gonioscopic imaging apparatus of claim 15, wherein the sensor used to capture the iridocorneal angle is also used to capture the iris, lens, or surrounding tissue.

18. The panoramic gonioscopic imaging apparatus of claim 1, wherein the objective optical device is configured such that light rays for imaging the iridocorneal angle are generally parallel with an optical axis of the panoramic gonioscopic imaging apparatus at the intermediate imaging plane.

19. An imaging system, comprising:
    a panoramic gonioscopic imaging apparatus comprising:
        a disposable component configured to rest against a cornea of a patient;
        an objective optical device configured to direct a continuous panoramic image of an entire circumference of an iridocorneal angle of the patient on an intermediate imaging plane; and
        a relay lens configured to direct the continuous panoramic image from the intermediate imaging plane to a sensor such that the sensor captures the entire circumference of the iridocorneal angle at once; and
    a computing device in communication with the panoramic gonioscopic imaging apparatus, the computing device configured to display an image of the entire circumference of the iridocorneal angle.

20. The imaging system of claim 19, wherein the computing device is configured to stack successive images of the entire circumference of the iridocorneal angle captured to increase signal strength in the displayed image.

* * * * *